United States Patent [19]

Lindel et al.

[11] Patent Number: 5,149,822
[45] Date of Patent: Sep. 22, 1992

[54] PREPARATION OF 2,3-DICHLORO-5-ACETYLPYRIDINE

[75] Inventors: Hans Lindel, Leverkusen; Werner Hallenbach, Langenfeld; Bernd Gallenkamp, Wuppertal, all of Fed. Rep. of Germany

[73] Assignee: Bayer Aktiengesellschaft, Leverkusen, Fed. Rep. of Germany

[21] Appl. No.: 336,969

[22] Filed: Apr. 12, 1989

[30] Foreign Application Priority Data

May 7, 1988 [DE] Fed. Rep. of Germany ....... 3815727
Nov. 11, 1988 [DE] Fed. Rep. of Germany ....... 3838243

[51] Int. Cl.$^5$ .................... C07D 211/70; C07D 211/82
[52] U.S. Cl. .................................................... 546/315
[58] Field of Search ........................................ 546/315

[56] References Cited

U.S. PATENT DOCUMENTS 3,591,642  7/1971  Szinai et al. ................. 546/315
4,358,455  11/1982  Atkinson et al. ............. 546/300

FOREIGN PATENT DOCUMENTS 3615293  11/1987  Fed. Rep. of Germany .
3723070  1/1989  Fed. Rep. of Germany .
2238264  10/1987  Japan ................................. 546/315

OTHER PUBLICATIONS

Fieser et al. Reagents for Org. Synthesis vol. I p. 522, 523, 688 (1967).

American Chemical Journal, vol. XIV. 1892, pp. 480–545.

*Primary Examiner*—Johann Richter
*Attorney, Agent, or Firm*—Sprung Horn Kramer & Woods

[57] ABSTRACT

A process for the preparation of 2,3-dichloro-5-acetylpyridine of the formula

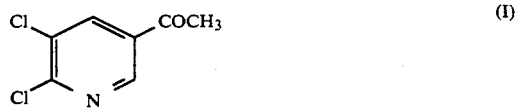

(I)

comprising decarboxylating a compound of the formula

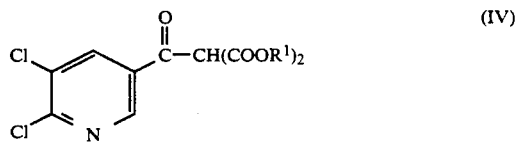

(IV)

in which $R^1$ stands for methyl or ethyl, in a mixture of water and a water miscible aprotic solvent.

4 Claims, No Drawings

PREPARATION OF 2,3-DICHLORO-5-ACETYLPYRIDINE

The present invention relates to new processes for the preparation of 2,3-dichloro-5-acetylpyridine and to intermediates for carrying out these processes and their preparation.

Pyridyl alkyl ketones and their use as intermediates for the preparation of pyridylethanolamines are described in U.S. patent application Ser. No. 40,509, filed Apr. 20, 1987, now pending.

In the process described therein, they are obtained by reacting alkyl nicotinates with alkyl acetates in a Claisen ester condensation and hydrolyzing and decarboxylating the pyridoylacetates thus obtained.

The pyridylethanolamines are active compounds for promoting the yield of animals.

The present invention relates to the following: 1. Process for the preparation of 2,3-dichloro-5-acetylpyridine of the formula (I)

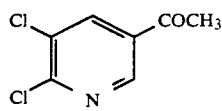

a) characterized in that 5,6-dichloronicotinoyl halide of the formula (II)

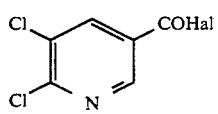

in which
Hal stands for halogen,
are reacted with malonic acid esters of the formula (III)

in which
$R^1$ stands for $C_{1-3}$-alkyl,
in the presence of magnesium compounds and bases and the products are then subjected to gentle decarboxylation in the presence of aqueous acids, or b) characterized in that compounds of the formula (IV)

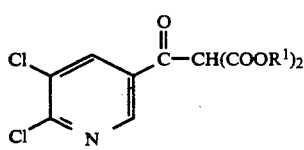

in which
$R^1$ stands for $C_{1-3}$-alkyl,
are decarboxylated in the presence of water, if appropriate in the presence of an organic solvent and if appropriate in the presence of a protonic acid, at temperature between 50° and 180° C., or c) characterized in that 5,6-dichloronicotinoyl halide of the formula (II)

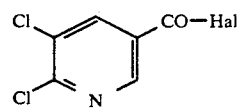

is reacted with a methylmagnesium halide of the formula (V)

$$H_3C\ MgHal \qquad (V)$$

in which
Hal stands for halogen,
in the presence of catalysts, or d) characterized in that 5,6-dichloronicotinic acid of the formula (VI)

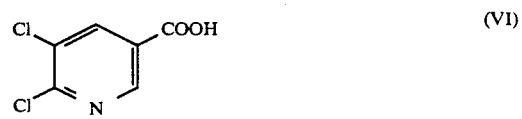

is reacted with methyllithium.

2. Compounds of the formula (IV)

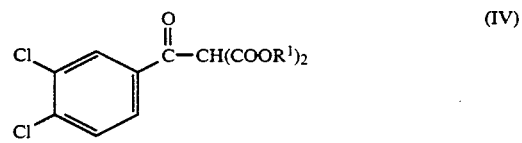

in which
$R^1$ stands for $C_{1-3}$-alkyl,
are new.

3. Process for the preparation of the compounds of the formula (IV) according to 2 (above), characterized in that compounds of the formula (II)

in which
Hal stands for halogen,
are reacted with malonic acid esters of the formula (III)

$$CH_2(COOR^1)_2 \qquad (III)$$

in which
$R^1$ stands for $C_{1-3}$-alkyl,
in the presence of magnesium salts and bases.

If 5,6-dichloronicotinoyl chloride is used as the compound of the formula (II) and dimethyl malonate is used as the compound of the formula (III) in process 1a), the process can be represented by the following equation:

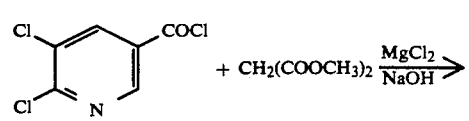

-continued

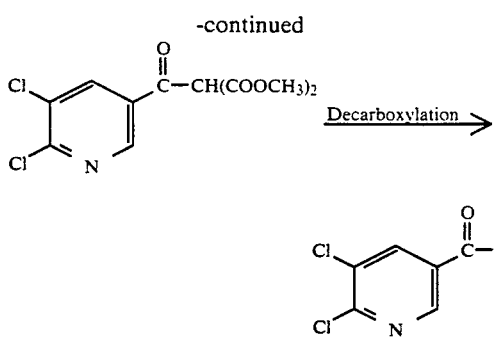

Compounds of the formula (II) are known (H. Meyer et al. Ber. Dt. Chem. Ges. 61 (1928), 2202). The following compounds of the formula (II) may be mentioned specifically: 5,6-dichloronicotinoyl chloride and 5,6-dichloronicotinoyl bromide.

Compounds of the formula (III) are known. Compounds which may be mentioned specifically are: dimethyl, diethyl and di-t-butyl malonate and Meldrum's acid.

The reaction is carried out by reacting the nicotinoyl halides with the malonates and magnesium salt in the presence of bases and diluents.

However, the nicotinoyl halides can also be reacted with the corresponding alkoxymagnesium malonates. Compounds of this type which may be mentioned are: dimethyl methoxymagnesium malonate and diethyl ethoxymagnesium malonate. These compounds are known, for example, from Org. Synth. Col. Vol. IV (1963) 285.

Magnesium salts which may be mentioned are: magnesium chloride, bromide, hydroxide, oxide and nitrate.

Bases which may be mentioned are: alkali metal and alkaline earth metal hydroxides, such as NaOH or KOH, tertiary amines, such as triethylamine, triethylenediamine and trimethylene-tetrahydropyrimidine, and alkali metal and alkaline earth metal alcoholates, such as Na methylate and K t-butylate.

Possible diluents are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl and dibutyl ether, glycol dimethyl ether and diglycol dimethyl ether, tetrahydrofuran and dioxane, and in addition esters, such as methyl and ethyl acetate, and furthermore nitriles, such as, for example, acetonitrile and propionitrile, benzonitrile and glutaric acid dinitrile, and moreover amides, such as, for example, dimethylformamide, dimethylacetamide and N-methylpyrrolidone, as well as tetramethylene sulfone, dimethylsulfoxide and hexamethylphosphoric acid triamide.

1 to 3 mols of malonate of the formula (III) are employed per mol of the nicotinoyl halide of the formula (II). 1 to 2 and preferably 1 to 1.5 mols of magnesium salt and 2 to 4, preferably 2–3 mol, of base are employed per mol of malonate of the formula (III).

The reaction is carried out at temperatures from −20° C. to 150° C., preferably from −10° C. to +60° C..

When the reaction has ended, the mixture is diluted with water and acidified and the nicotinoyl malonate formed is extracted.

The nicotinoyl malonate of the formula (IV) is decarboxylated in the presence of water and, if appropriate, in the presence of protonic acids at temperatures between 50° and 180° C.

If dimethyl 5,6-dichloronicotinoyl-malonate is used as the compound of the formula (IV) in process 1b, the process can be represented by the following equation:

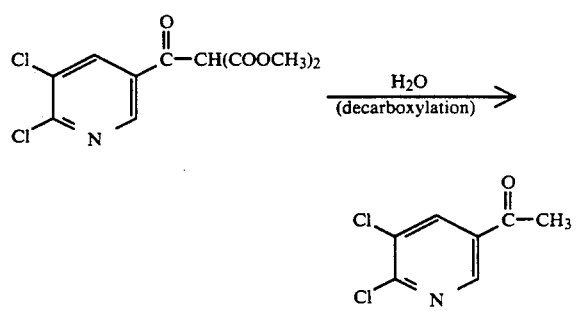

The reaction is carried out by heating the nicotinoyl malonate in the presence of water.

Protonic acids which may be mentioned are hydrochloric acid, sulfuric acid, phosphoric acid, hydrobromic acid, toluenesulfonic acid, methanesulfonic acid and acid ion exchanger resins.

The reaction is preferably carried out in the presence of water-miscible organic diluents.

Such diluents which may be mentioned are lower aliphatic carboxylic acids, such as formic acid or acetic acid, dioxane, ethylene glycol dimethyl ether, diethylene glycol diethyl ether, dimethyl formamide, dimethylsulfoxide sulfolane and N-methylpyrrolidone.

The reaction is carried out at temperatures between about 50° and 180° C., preferably between 70° C. and 160° C.

Working-up is carried out according to standard methods (cf. examples).

If 5,6-dichloronicotinoyl chloride is used as the compound of the formula (II) and methylmagnesium chloride is used as the compound of the formula (V) in process 1c), the process can be represented by the following equation:

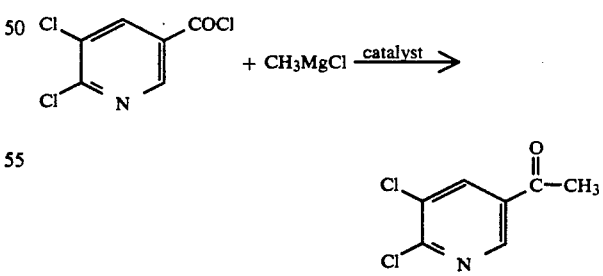

The compounds of the formula (V) are known. Compounds which may be mentioned specifically are methylmagnesium chloride and methylmagnesium bromide.

The reaction is carried out by reacting the nicotinoyl halides and methylmagnesium halide in the presence of a catalyst in a diluent.

Catalysts which may be mentioned are iron(II) chloride and tris-(2,4-pentanedionato)-iron.

Possible diluents are virtually all the inert organic solvents.

These include, in particular, aliphatic and aromatic hydrocarbons, such as pentane, hexane, heptane, cyclohexane, petroleum ether, benzine, ligroin, benzene and toluene, and furthermore ethers, such as diethyl and dibutyl ether, glycol dimethyl ether and diglycol dimethyl ether, tetrahydrofuran and dioxane.

0.8 to 1 mol of methylmagnesium halide of the formula (V) and 1 to 10 mol % of catalyst are employed per mol of the nicotinoyl halide of the formula (II).

The reaction is carried out at temperatures from $-100°$ C. to $+50°$ C., preferably $-80°$ C. to $20°$ C.

The mixture is worked up in the manner customary for Grignard reactions.

Process 1d) can be represented by the following equation:

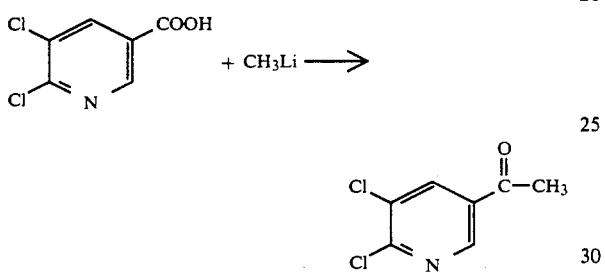

5,6-Dichloronicotinc acid is known (H. Meyer and R. Graf, Ber. Dt. Chem. Ges. 61, (1928), 2022). Methyllithium is known.

The reaction is carried out by reacting the nicotinic acid with methyllithium in a diluent.

Possible diluents are virtually all the inert organic solvents.

These include, in particular, aliphatic and aromatic hydrocarbons, such as pentane, hexane, heptane, cyclohexane, petroleum ether, benzine, ligroin, benzene and toluene, and furthermore ethers, such as diethyl and dibutyl ether, glycol dimethyl ether and diglycol dimethyl ether, tetrahydrofuran and dioxane.

2 to 4 mols of methyllithium are employed per mol of nicotinic acid of the formula (VI).

The reaction is carried out at temperatures from $-100°$ C. to $+50°$ C., preferably from $-90°$ C. to $0°$ C.

The mixture is worked up in the manner customary for reactions with organolithium compounds.

The new compounds of the formula (VI) are prepared by the reaction, described in process 1a), of nicotinoyl halides of the formula (II) with malonates of the formula III.

The 2,3-dichloro-5-acetylpyridine of the formula (I) obtainable by processes 1a–d) according to the invention is used for the preparation of pyridylethanolamine derivatives.

For this, the dichloroacetylpyridine is converted by means of ammonia into amino-chloro-acetyl-pyridine, which is reacted with elemental halogen or with copper halides. The halogenomethyl pyridyl ketone thus obtained is reacted with amines and the products are then reduced. This reaction can be illustrated by the following equation:

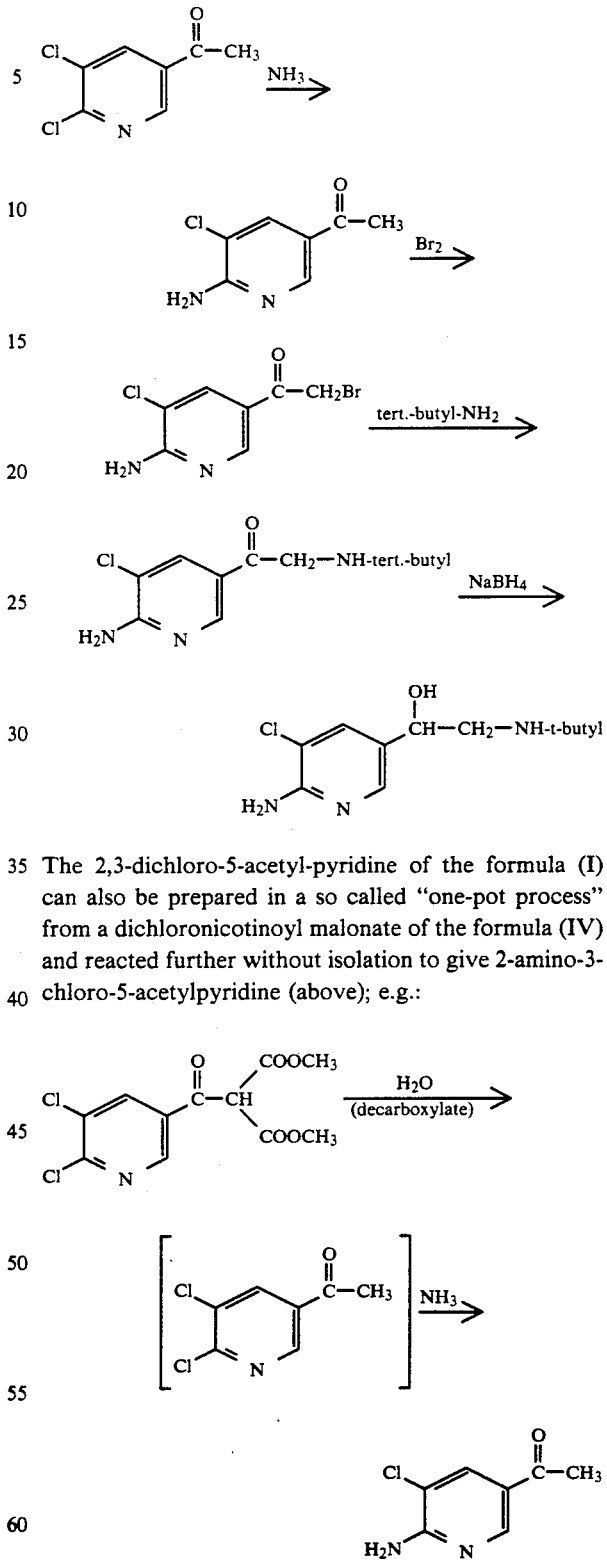

The 2,3-dichloro-5-acetyl-pyridine of the formula (I) can also be prepared in a so called "one-pot process" from a dichloronicotinoyl malonate of the formula (IV) and reacted further without isolation to give 2-amino-3-chloro-5-acetylpyridine (above); e.g.:

The halogenomethyl ketones can also first be reduced and then reacted with the amine.

The procedure for the subsequent reactions is described in U.S. patent application Ser. No. 40,509, supra.

PREPARATION EXAMPLES

Examples of process 1a (1st stage) and 2

Example 1

1.43 g (15 mmol) of anhydrous $MgCl_2$ are added to 10 ml of dry acetonitrile at 0° C. When the exothermic reaction has subsided, 1.7 ml (15 mmol) of dimethyl malonate and then 4.2 ml (30 mmol) of triethylamine are added and the mixture is stirred at 0° C. for 15 minutes. 2.63 g (12.5 mmol) of 5,6-dichloronicotinoyl chloride (prepared by the method of H. Meyer and R. Graf, Ber. dt. Chem. Ges. 61 (1928) 2202), dissolved in 3 ml of methylene chloride, are then added dropwise to the mixture. The mixture is stirred at 0° C. for a further hour and then at room temperature for two hours. For working up, it is poured into 50 ml of 1N hydrochloric acid and extracted with methylene chloride and the extract is washed with saturated NaCl solution. After drying with $Na_2SO_4$, the extract is evaporated.

Residue: 3.68 g (96% of theory).
Melting point: 99° C.

Example 2

Diethyl 5,6-dichloro-nicotinoyl-malonate is obtained analogously as an oil in a purity of 90%

Example of the use of NaOH/MgO as the base

Example 3

8.4 ml (55 mmol) of diethyl malonate are initially introduced into 25 ml of dry dimethylformamide at 0° C. and 6.6 g (55 mmol) of a finely powdered mixture of one part by weight of MgO and two parts by weight of NaOH are introduced. The mixture is stirred at 0° C. for a further 15 minutes and 5.3 g (25 mmol) of 5,6-dichloronicotinoyl chloride, dissolved in 5 ml of dry methylene chloride, are then added dropwise at 0° C. The mixture is then stirred at 0° C. for one hour and subsequently at room temperature for a further two hours. For working up, the entire mixture is poured into 150 ml of 2N HCl solution and extracted with methylene chloride. The combined extracts are washed several times with saturated NaCl solution, dried with $Na_2SO_4$ and evaporated.

Residue: 7.0 g of yellow oil.
Content of diethyl 5,6-dichloronicotinoyl malonate: 67%.

Example of the use of K tert.-butylate as the base

Example 4

2.86 g (30 mmol) of anhydrous $MgCl_2$ are initially introduced into 10 ml of dry acetonitrile. 4.6 ml (30 mmol) of diethyl malonate are then added at 0° C. and 6.75 g (60 mmol) of K tert.-butylate are subsequently introduced in portions at 0° C. A solution of 6.25 g (25 mmol) of 5,6-dichloro-nicotinoyl chloride, dissolved in 10 ml of dry methylene chloride, is added dropwise to this mixture at 0° C. The mixture is subsequently stirred first at 0° C. for one hour and then at room temperature for two hours and is then poured into 150 ml of 2N HCl solution, extracted several times with methylene chloride, dried with $Na_2$—$SO_4$ and evaporated.

Residue: 9.1 g of yellow oil.
Content of diethyl 5,6-dichloronicotinoyl malonate: 42%.

Example of processes 1a (2nd stage) and 1b

Example 5

5-Acetyl-2,3-dichloropyridine 30.4 g (content 90%, 82 mmol) of diethyl 5,6-dichloronicotinoyl malonate are added to a mixture of 123 ml of glacial acetic acid, 77 ml of water and 4.45 g (45 mmol) of 96% strength $H_2SO_4$ and the entire mixture is heated to 100° C. After 120 minutes, about 90% of the malonate has reacted. The mixture is cooled, poured into 500 ml of water and extracted with methylene chloride and the extract is washed twice with 1N sodium hydroxide solution. After drying with $Na_2SO_4$, the extract is evaporated.

Yield: 9.3 g (60% of theory).
Melting point: 80° C.

Example of the use of dioxane

Example 6

3.04 g (7.3 mmol) of diethyl 5,6-dichloronicotinoyl malonate (content 80%) are added to a mixture of 17 ml of dioxane, 7.5 ml of $H_2O$ and 970 mg (9.1 mmol) of $H_2SO_4$ and the entire mixture is heated under reflux for 5 hours. For working up, the mixture is neutralized with NaOH and evaporated and the residue is taken up in 100 ml of 10% strength NaOH. The mixture is extracted with methylene chloride and the extract is washed with 10% strength $NaH_2PO_4$ solution and, after drying with $Na_2SO_4$, evaporated.

Residue: 1.1 g (79.5% of theory).
Melting point: 80° C.

Example of the use of dimethyl sulfoxide

Example 7

A mixture of 15.3 g (0.048 mol) of dimethyl 5,6-dichloronicotinoyl malonate (96.5 % pure), 1.8 g (0.10 mol) of water and 50 ml of dimethyl sulfoxide is stirred for 3 hours at a bath temperature of 150° C. and then poured into 125 ml of water. The organic phase is separated off and diluted with 100 ml of methylene chloride. The aqueous phase is extracted with methylene chloride. The combined methylene chloride phases are dried with sodium sulphate and filtered. The solvent is distilled off carefully from the filtrate in a water-jet vacuum. 10.9 g of a crude product are obtained which, according to GC/MS analysis, contains 83% of 2,3-dichloro-5-acetylpyridine (99% of theory) and 12% of dimethyl sulfoxide as well as 3% of 2-chloro-5-acetylpyridine.

Example of process 1c

Example 8

310 mg (0.88 mmol) of tris-(2,4-pentanedionato)-iron are added to a solution of 3.7 g (17.6 mmol) of 5,6-dichloronicotinoyl chloride in 36 ml of dry tetrahydrofuran, and 5 ml (15 mmol) of a 3 molar solution of methylmagnesium chloride in tetrahydrofuran are then added dropwise at −20° C. over a period of 30 minutes. The mixture is subsequently stirred at −20° C. for a further 20 minutes and is then poured into 300 ml of 1N HCl and extracted exhaustively with methylene chloride. The combined extracts are washed successively with 2N NaOH and then with 5% strength $NaH_2PO_4$ solution, dried with $Na_2SO_4$ and evaporated.

Residue: 1.75 g (61% of theory, based on the methylmagnesium chloride employed).

Melting point: 78° C.

Example of process 1d

Example 9

62 ml of a 1.6 M solution (100 mmol) of methyllithium in ether are added to a solution of 9.6 g (50 mmol) of 5,6-dichloronicotinic acid in 250 ml of absolute ether at 0° C. When the addition has ended, the mixture is subsequently stirred at 0° C. for a further 30 minutes and 200 ml of water are then added, while cooling with ice. The phases are separated and the aqueous phase is extracted once more with 50 ml of ether. The combined organic phases are dried over sodium sulphate and evaporated. 9 g (95% of theory) of 2,3-dichloro-5-acetylpyridine, melting point 80° C., are obtained.

Examples of the further reaction of the 5,6-dichloroacetylpyridine to give substituted pyridylethanolamines

Example a (aminolysis)

2-Amino-3-chloro-5-acetylpyridine

Variant α

1.9 g (10 mmol) of 2,3-dichloro-5-acetylpyridine are heated at 170° C. in a mixture of 80 ml of tetrahydrofuran and 20 ml of concentrated aqueous ammonia in an autoclave for 8 hours. After the tetrahydrofuran has been evaporated off, the residue is diluted with water, brought to pH 5 and extracted with ethyl acetate.
Yield: 1.65 g (97%), melting point: 188° C.

Variant β

A mixture of 72.3 g (0.38 mol) of 2,3-dichloro-5-acetylpyridine and 380 ml of dimethyl sulfoxide is heated to 70° C. and at this temperature 760 ml of a concentrated aqueous ammonia solution are added dropwise. The reaction mixture is stirred at 100° C. for 19 hours and cooled to 15° C. The product obtained incristalline form is isolated by suction filtration.
Yield: 53.1 g (82% of theory), m.p. 188° C.

Variant γ

A mixture of 19.0 g (0.10 mol) of 2,3-dichloro-5-acetylpyridine, 300 ml of isopropanol and 110 ml of a concentrated aqueous ammonia solution is stirred in an autoclave for 5 hours at 170° C. It is then evaporated, the residue is stirred with 400 ml of water for 30 minutes and the product obtained in cristalline form is isolated by suction filtration.
Yield: 16.5 g (97% of theory), m.p. 188 ° C.

Variant δ

A mixture of 15,3 g (0.0483 mol) of dimethyl 2,3-dichloro-5-nicotinoylmalonate, 50 ml of dimethyl sulfoxide and 1.8 g of water is stirred for 3 hours at 150° C. After cooling the mixture to 90° C., 100 ml of a concentrated aqueous ammonia solution are added dropwise. The reaction mixture is stirred for 18 hours at 100° C. and then cooled to 15° C. The product thus obtained in cristalline form is isolated by suction filtration.
Yield: 6.6 g (80% of theory).

Example b (halogenation)

2-Amino-3-chloro-5-pyridyl bromomethyl ketone 16 g (0.1 mol) of bromine are added dropwise to a solution of 17.05 g (0.1 mol) of 2-amino-3-chloro-5-acetylpyridine in a mixture of 19.3 g of hydrogen bromide (47% strength aqueous solution; 0.11 mol) and 500 ml of glacial acetic acid. The mixture is subsequently stirred for a further two hours, brought to pH 8 and extracted with ethyl acetate. Drying and evaporation give 18.5 g (74%) of the title compound of melting point 134° C.

Example c (Reaction of the pyridyl halogenoalkyl ketone with amines)

2-Amino-3-chloro-5-pyridyl isopropylaminomethyl ketone 9.98 g (0.04 mol) of the compound prepared under Example b are introduced in portions into a solution of 11.8 g (0.2 mol) of isopropylamine in 150 ml of methanol at 0° C. The mixture is allowed to come to room temperature and is subsequently stirred for a further 2 hours and evaporated. The residue is taken up in buffer of pH 5 and the mixture is washed with ether. The aqueous phase is brought to pH 9 and extracted with ethyl acetate. After drying and evaporation, 6.8 g (75%) of the title compound are obtained as an amorphous powder.

Example d (Reduction of the pyridylaminoalkyl ketone)

1-(2-Amino-3-chloro-5-pyridyl)-2-isopropylaminoethanol 0.38 g (10 mmol) of sodium borohydride is added in portions to a solution of 2.28 g (10 mmol) of the compound prepared according to Example c in 50 ml of methanol at 0° C. The mixture is allowed to come to room temperature and is brought to pH 1 with dilute hydrochloric acid and evaporated. The residue is taken up in water and washed with ether. The mixture is then brought to pH 10 and extracted with ethyl acetate. Drying and evaporation give 2.1 g (92%) of the title compound of melting point 146° C.

It will be appreciated that the instant specification and claims are set forth by way of illustration and not limitation, and that various modifications and changes may be made without departing from the spirit and scope of the present invention.

What is claimed is:

1. A process for the prepartion of 2,3-dichloro-5-acetylpyridine of the formula

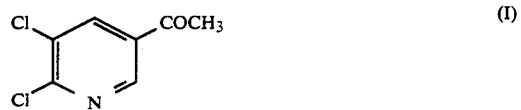

(I)

comprising
decarboxylating a compound of the formula

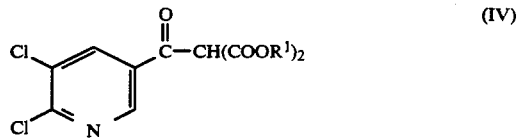

(IV)

in which
R¹ stands for methyl or ethyl,
in a solvent selected from the group consisting of (a) dimethylsulfoxide and water, and (b) dioxane, acid and water.

2. A process according to claim 1, wherein the mixture of water and solvent contains a protonic acid.

3. A process according to claim 1, wherein the aprotic solvent comprises dimethyl sulfoxide.

4. A process according to claim 1, wherein the solvent comprises dioxane, acid and water.

* * * * *